United States Patent

Hannart et al.

Patent Number: 4,719,208
Date of Patent: Jan. 12, 1988

[54] 1,2,3,4,5,6-HEXAHYDROAZEPINO(4,5-B)INDOLE DERIVATIVES, THEIR PREPARATION, INTERMEDIATE COMPOUNDS, AND THEIR APPLICATION IN THERAPEUTICS

[75] Inventors: Jean-Alfred A. Hannart, Dion-Valmont; Jean-Paul Dejonghe, Wavre; Danielle De Campeneere, Rixensart; Jean-Marie Maloteaux, Les Bons Villers, all of Belgium

[73] Assignee: Omnichem Societe Anonyme, Brussels, Belgium

[21] Appl. No.: 861,524

[22] Filed: May 9, 1986

[30] Foreign Application Priority Data

May 10, 1985 [LU] Luxembourg .................. 85894

[51] Int. Cl.$^4$ .................. A61K 31/55; C07D 487/04
[52] U.S. Cl. .................. 514/215; 540/521; 540/580
[58] Field of Search .................. 540/521, 580; 514/215

[56] References Cited

U.S. PATENT DOCUMENTS 3,419,569 12/1968 Renner .................. 540/580
3,525,750 8/1970 Renner .................. 540/580

Primary Examiner—Robert T. Bond
Attorney, Agent, or Firm—Fishman & Dionne

[57] ABSTRACT

The invention is related to new 1,2,3,4,5,6-hexahydro-5-hydroyalkylazepino[4,5-b]-indole derivatives, of formula:

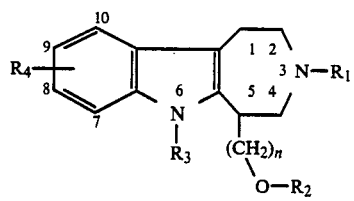

in which $R_1$ denotes a hydrogen atom, an alkyl radical, an alkenyl radical, a benzyl radical, an alkylamino radical of the type

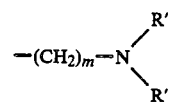

where the groups R' are either hydrogen atoms or alkyl radicals or form, together with the nitrogen atom to which they are attached, a heterocyclic nucleus of the morpholinyl, piperidinyl, pyrrolidinyl or piperazinyl type, and m is 2 or 3, $R_2$ denotes a hydrogen atom or a benzoyl or acyl radical, $R_3$ denotes a hydrogen atom or an alkyl or benzyl radical, $R_4$ denotes a hydrogen or halogen atom, an alkyl radical an alkoxy radical or a trifluoromethyl radical, and n is 1 or 2, and the salts of addition to pharmaceutically acceptable acids, and to process for their preparation, to intermediates obtained and to their therapeutical use in treating mental disorders.

22 Claims, No Drawings

1,2,3,4,5,6-HEXAHYDROAZEPINO(4,5-B)INDOLE DERIVATIVES, THEIR PREPARATION, INTERMEDIATE COMPOUNDS, AND THEIR APPLICATION IN THERAPEUTICS

The present invention relates to 1,2,3,4,5,6-hexahydroazepino[4,5-b]indole derivatives, their preparation and their application in therapeutics. It also extends to the intermediate products obtained during their preparation.

The present invention relates to pharmaceutical compositions whose subject is 1,2,3,4,5,6-hexahydro-5-hydroxyalkylazepino[4,5-b]indole derivatives, optionally in the form of salts of addition to a therapeutically acceptable acid corresponding to the formula I

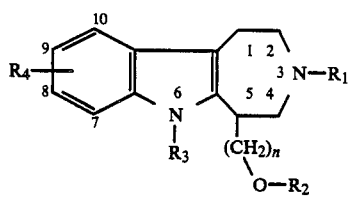

in which n is 1 or 2,

R₁ denotes a hydrogen atom, an alkyl radical, an alcenyl radical, a benzyl radical, an alkylamino radical of the type

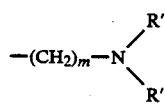

where the groups R' are either hydrogen atoms or alkyl radicals or form, together with the nitrogen atom to which they are attached, a heterocyclic nucleus of the morpholinyl, piperidinyl, pyrrolidinyl or piperazinyl type, and m is 2 or 3, R₂ denotes a hydrogen atom, or a benzoyl or acyl radical, R₃ denotes a hydrogen atom, or an alkyl or benzyl radical, R₄ denotes a hydrogen or halogen atom, an alkoxy radical or a trifluoromethyl radical, the terms "alkyl" and "alkoxy" containing from 1 to 4 and the term "acyl" from 2 to 4 carbon atoms.

Among the abovementioned derivatives, there may be especially mentioned:

1,2,3,4,5,6-hexahydro-5-hydroxymethylazepino[4,5-b]indole, 1,2,3,4,5,6-hexahydro-3-methyl-5-hydroxymethylazepino[4,5-b]indole, 1,2,3,4,5,6-hexahydro-3-ethyl-5-hydroxymethylazepino[4,5-b]indole, 1,2,3,4,5,6-hexahydro-3-propyl-5-hydroxymethylazepino[4,5-b]indole, 1,2,3,4,5,6-hexahydro-5-hydroxymethyl-6-methylazepino[4,5-b]indole, 1,2,3,4,5,6-hexahydro-3,6-dimethyl-5-hydroxymethylazepino[4,5-b]indole, 1,2,3,4,5,6-hexahydro-3-ethyl-5-hydroxymethyl-6-methylazepino[4,5-b]indole, 1,2,3,4,5,6-hexahydro-3-methyl-5-hydroxymethyl-6-ethylazepino[4,5-b]indole, and 1,2,3,4,5,6-hexahydro-3-ethyl-5-hydroxyethylazepino[4,5-b]indole.

The starting raw material for the preparation of derivatives I where n=1 is 1,2,3,4,5,6-hexahydro-5-carboalkoxy azepino[4,5-b]indole of formula IIa

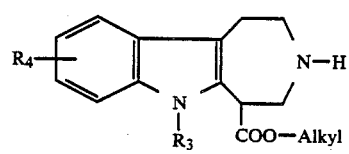

where R₃ and R₄ have the meaning referred to above.

Various synthetic approaches for the preparation of the product IIa have been described by Kuehne in the following patents: U.S. Pat. No. 4,154,843 of 15 May 1979, U.S. Pat. No. 4,267,330 of 12 May 1981, U.S. Pat. No. 4,283,536 of 11 Aug. 1981 and U.S. Pat. No. 4,362,739 of 7 Dec. 1982.

The starting raw material for the preparation of the derivatives I where n=2 is 1,2,3,6-tetrahydro-5-carbomethoxymethyleneazepino[4,5-b]indol-4-one of formula IIb

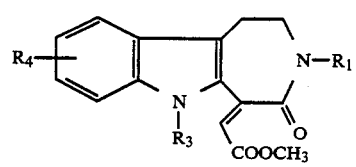

where R₁, R₃ and R₄ have the meaning referred to above. These products may be prepared from substituted tetrahydro-β-carboline. The compounds I, where n=1, of the present invention may be prepared by two procedures.

First procedure

This procedure first comprises the reduction of the carboalkoxy group of product IIa, followed by substitution of the nitrogen in position 3, according to the following general scheme:

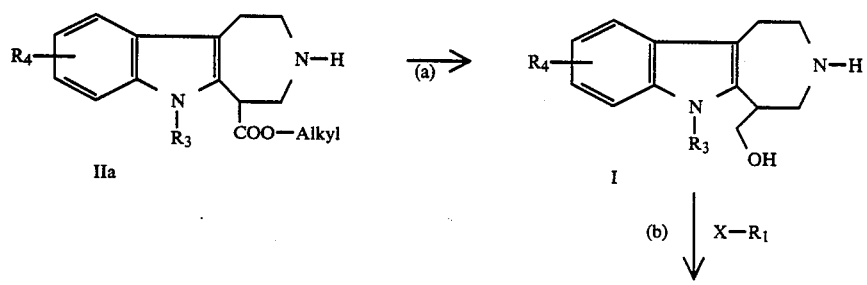

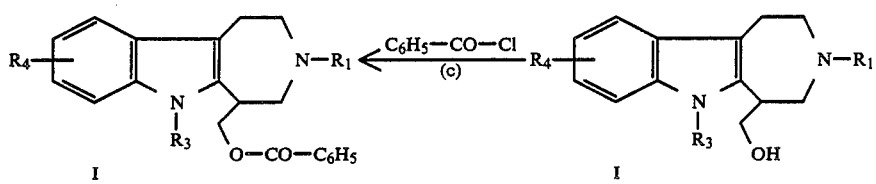

where $R_1$, $R_3$ and $R_4$ have the meaning referred to above, and X denotes a halogen atom.

Stage (a) of the reduction of the carboalkoxy group of compound IIa may be carried out in an inert organic solvent, for example tetrahydrofuran. The reaction temperature may be between 20° C. and the reflux temperature of the solvent. The reducing agent may be lithium aluminium hydride.

The alkylation stage (b) may be carried out in a conventional manner by the condensation of an alkyl, benzyl or substituted or unsubstituted alkylamino halide, in the presence of a tertiary amine such as diisopropylethylamine or triethylamine in a chlorinated aliphatic hydrocarbon such as chloroform or dichloroethane. The reaction temperature may be between 20° C. and the reflux temperature of the solvent.

The benzoylation or acylation stage (c) may be carried out in a conventional manner by the concensation of benzoyl chloride or acid chloride in the presence of pyridine in a chlorinated aliphatic hydrocarbon such as chloroform or dichloroethane, at ambient temperature.

Second procedure

This procedure first comprises the substitution of the nitrogen in position 3 of the product IIa, followed by the reduction of the carbomethoxy group according to the following scheme:

(1) Preparation of derivatives I where $R_1$ is an alkyl radical, an alkenyl radical or a benzyl radical.

where $R_3$ and $R_4$ have the meaning referred to above.

Procedure (a) involves the condensation of an aliphatic or aromatic aldehyde with the product IIa, to form the methanoazepinoindoles of formula III, in accordance with the method described by Kuehne in U.S. Pat. No. 4,362,739 of 7 Dec. 1982. The reduction of III to IV may be carried out in an organic solvent such as methanol or ethanol, in an acidic medium at normal temperature. The reducing agent may be sodium cyanoborohydride.

Procedure (b) involves the condensation of an alkyl, alcenyl or benzyl halide with the product IIa, to form the product IV. The condensation reaction may be carried out in a conventional manner in the presence of a tertiary amine such as diisopropylethylamine or triethylamine, in a chlorinated aliphatic hydrocarbon such as chloroform or dichloroethane.

Procedure (b) may also involve the condensation of an alkyl chloroformate or an acid chloride. In this case, the reaction is carried out in a binary system consisting of a solution of product IIa in ethyl acetate and an aqueous caustic soda solution, to form the product IV where $R_1$ is a —COO-alkyl or —CO-alkyl group.

The reduction of product IV to product I is performed in accordance with the method described in the first procedure, using lithium aluminium hydride.

(2) Preparation of derivatives I where $R_1$ is an alkylamino radical.

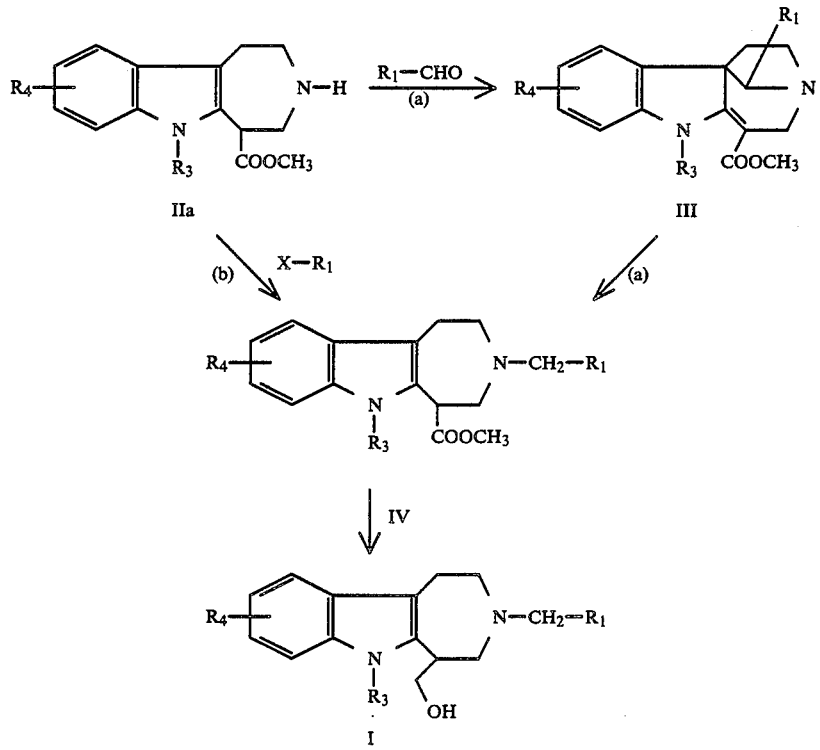

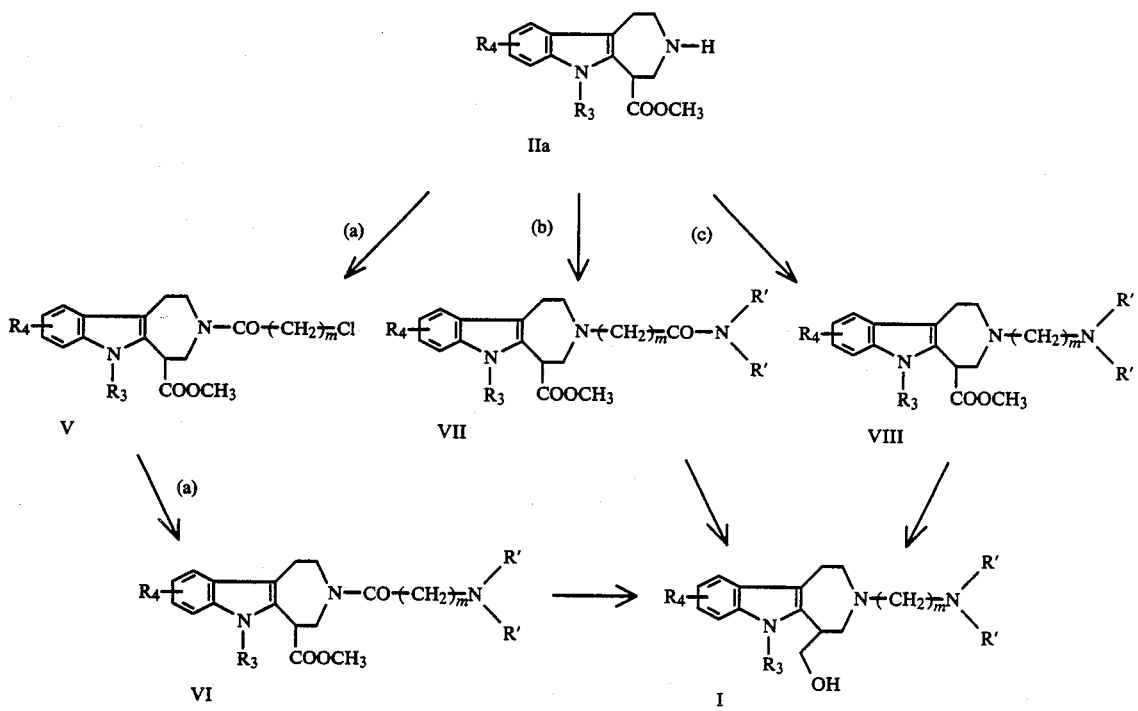

where $R_3$ and $R_4$ have the meanings referred to above.

Procedure (a) is carried out by the addition of an acid chloride of the type X—(CH$_2$)$_m$—COCl where X is a bromine or chlorine atom and m=1 or 2, to a binary system consisting of a solution of product IIa in ethyl acetate and an aqueous caustic soda solution. Product V is then condensed with primary or secondary amines in an organic solvent such as tetrahydrofuran, to give product VI.

Procedure (b) is carried out by the addition of chloroamides of the type

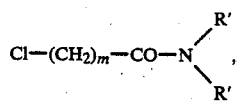

where m=1 or 2, to product IIa in the presence of a tertiary amine such as diisopropylethylamine or triethylamine, either in a chlorinated aliphatic hydrocarbon such as chloroform or dichloroethane, or in the presence of potassium carbonate in methyl ethyl ketone, to give product VII.

Procedure (c) is carried out in a conventional manner by the condensation of an alkyamine halide of the type

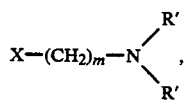

where X is a chlorine or bromine atom and m=2 or 3, with product IIa in the presence of a tertiary amine such as diisopropylethylamine or triethylamine, in a chlorinated aliphatic hydrocarbon such as chloroform or dichloroethane, to give product VIII.

The reduction of products VI, VII and VIII to product I is carried out in accordance with the method described in the first procedure, using lithium aluminium hydride.

The compounds I, where n=2, of the present invention may be prepared according to the following procedure:

The procedure first comprises the catalytic reduction of the carboxymethylene group of product IIb to product IX, followed by the reduction of the carbomethoxy group to product I, according to the following general scheme:

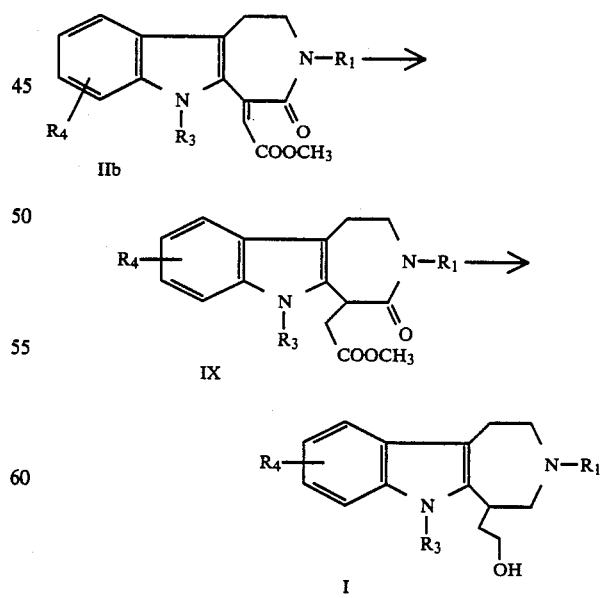

The reduction of IIb may be carried out in a conventional manner by means of a catalytic hydrogenation using palladium-containing charcoal. The catalytic hydrogenation may be carried out in a suitable solvent, for example acetic acid, at temperatures of between 20° C. and 40° C. The reduction of the carbomethoxy group and of the oxo group is carried out in accordance with the method described in the first procedure, using lithium aluminium hydride.

The pharmacological study of the compounds of the invention shows that they are active in three hypoxia tests: hypobaric hypoxia, histotoxic, KCN-induced hypoxia and normobaric nitrogen hypoxia.

Since the compounds of the invention possess an antianoxic action, they may be used in therapeutics for the treatment of vigilance disorders, especially for combatting behavioural disorders attributable to cerebral vascular damage and to cerebral sclerosis in geriatrics.

The invention consequently comprises all pharmaceutical compositions containing the compounds and/or their salts as active principles, in combination with any excipients suitable for their administration, especially orally or parenterally.

The daily dosage may range from 10 to 100 mg.

The following examples illustrate the characteristics of the invention in a nonlimiting manner.

EXAMPLE 1

1,2,3,4,5,6-hexahydro-5-hydroxymethylazepino[4,5-b]indole (I: $R_1$, $R_2$, $R_3$, $R_4$=H; n=1)

A solution of 24.43 g (0.1 mol) of 5-carbomethoxyazepino[4,5-b]indole dissolved in 300 ml of tetrahydrofuran, is added dropwise under argon to a suspension of 3.9 g (0.102 mol) of lithium aluminium hydride in 250 ml of tetrahydrofuran.

The reaction mixture is stirred for 2 hours at ambient temperature. It is then treated with water-saturated magnesium sulphate. The mixture is stirred for an hour and is then filtered on dicalite. The precipitate is rinsed with 50 ml of tetrahydrofuran.

The filtrate is then evaporated under vacuum and the residue is taken up in 300 ml of methylene chloride, washed twice with a saturated salt solution and is dried over magnesium sulphate. After filtration and evaporation, 15.6 g of an organic material are obtained, which are purified by chromatography on silica (elution with $CH_2Cl_2$/2% MeOH). The residue is crystallized from methanol and yields 12.9 g of product.

Yield: 60%.

M.p.: 149° C.

U.V. (MeOH)$\lambda_{max}$: 224, 282, 291 nm

M.S. m/e (%): 216 (89 M+), 198 (16), 186 (28), 174 (92), 168 (17), 156 (100), 144 (56), 130 (33), 115 (14).

I.R. (KBr): 3300, 2900, 1623, 1462, 1347, 1094, 1022, 831 cm$^{-1}$

N.M.R. (CDCl$_3$)δ: 8.56 (m, 1H), 7.46-6.76 (m, 4H), 3.73 (m, 4H), 3.33-2.43 (m, 7H).

EXAMPLE 2

1,2,3,4,5,6-hexahydro-3-methyl-5-hydroxymethylazepino[4,5-b]indole (I: $R_1$=CH$_3$; $R_2$, $R_3$, $R_4$=H; n=1)

(a) 1,2,3,4,5,6-hexahydro-3,5-dicarbomethoxyazepino[4,5-b]indole (IV: $R_1$=COOCH$_3$; $R_3$, $R_4$=H)

80 ml of 2M caustic soda are added to a solution of 6.1 g (0.025 mol) of 5-carbomethoxyazepino[4,5-b]indole in 100 ml of ethyl acetate followed, with good stirring, by 3.543 g (0.0375 mol) of methyl chloroformate dissolved in 10 ml of ethyl acetate. After 10 minutes' stirring, the reaction is finished. The organic phase is separated off and the aqueous phase is extracted twice with 50 ml portions of ethyl acetate. The organic phases are combined, washed with water, dried over magnesium sulphate and evaporated to dryness. The residue is crystallized from methanol and yields 5.9 g of product.

Yield: 70%

U.V. (MeOH)$\lambda_{max}$: 220, 284 nm

M.S. m/e (%): 302 (36)M+, 270 (100), 214 (66), 183 (17), 154 (21).

I.R. (KBr): 3460, 3000, 2450, 1730, 1690, 1480, 1460, 1440, 1410 cm$^{-1}$ (b) A solution of 5.5 g (0.0182 mol) of the azepinoindole prepared in (a) dissolved in 10G ml of tetrahydrofuran, is added dropwise under argon to a suspension of 1.38 g (0.0364 mol) of lithium hydride in 100 ml of tetrahydrofuran. A treatment similar to that described in example 1 makes it possible to isolate 4.1 g of an organic residue which, after crystallization from methanol, yields 3.03 g of product.

Yield: 72.3%

U.V. (MeOH)$\lambda_{max}$: 290, 283, 223 nm

M.S. m/e (%): 230 M+

I.R. (KBr): 3460, 3400, 3200, 3000, 2900, 1460, 1335, 1123 cm$^{-1}$.

N.M.R. (CDCl$_3$)δ: 8.03 (bs, 1H), 7.50-6.76 (m, 4H), 4.61 (m, 1H), 3.90 (m, 2H), 3.20-2.32 (m, 10H) incl. 2.43 (s, 3H).

EXAMPLE 3

1,2,3,4,5,6-hexahydro-3-ethyl-5-hydroxymethylazepino[4,5-b]indole (I: $R_1$=C$_2$H$_5$; $R_2$, $R_3$, $R_4$=H; n=1)

(a) 1,2,3,4,5,6-hexahydro-3-acetyl-5-carbomethoxyazepino[4,5-b]indole. (IV: $R_1$=COCH$_3$; $R_3$, $R_4$=H)

6 g (0.024 mol) of 5-carbomethoxyazepino[4,5-b]indole are suspended in 350 ml of ethyl acetate. After adding 350 ml of 2M caustic soda, 2.88 g (0.0368 mol) of acetyl chloride, dissolved in 30 ml of ethyl acetate, are added with intensive stirring.

A treatment similar to that described in example 2 (a) makes it possible to isolate 6.1 g of an organic material which, after crystallization from ethyl acetate, yields 5.7 g of product.

Yield: 80.8%

(b) In accordance with the procedure described in example 1, 3.5 g of product are obtained from 9.5 g of the product prepared in (a).

Yield: 43%

M.p.: 144.5° C.

U.V. (MeOH)$\lambda_{max}$: 291, 283 nm

M.S. m/e (%): 244 (M+ 51), 229 (25), 186 (14), 157 (100), 144 (14), 130 (11), 71 (51).

I.R. (KBr): 3237, 3063, 2910, 2840, 1465, 1344, 1203, 1067 cm$^{-1}$

N.M.R. (CDCl$_3$)δ: 8.40 (bs, 1H), 7.56-6.83 (m, 4H), 5.60 (bs, 1H), 4.03-3.56 (m, 2H), 3.33-2.26 (m, 9H) incl. 1.10 (tr, 3H).

EXAMPLE 4

1,2,3,4,5,6-hexahydro-3-propyl-5-hydroxymethylazepino[4,5-b]indole (I: $R_1$=C$_3$H$_7$; $R_2$, $R_3$, $R_4$ H; n=1)

(a) 1,2,3,4,5,6-hexahydro-3-propyl-5-carbomethoxyazepino[4,5-b]indole (IV: $R_1$=C$_3$H$_7$; $R_3$, $R_4$=H)

A solution of 6.5 g (0.026 mol) of 5-carbomethoxyazepino[4,5-b]indole and of 2 g (0.034 mol) of propionaldehyde in 130 ml of methanol is stirred at ambient temperature for 4 hours. Methanol and excess aldehyde are then distilled off under vacuum. The residue is dissolved in 130 ml of methanol. After the addition of 3.25 g (0.026 mol) of benzoic acid and of 3.25 g (0.0157 mol) of sodium cyanoborohydride, the mixture is stirred for 10 hours at ambient temperature. After evaporation of the solvent, the residue is taken up in 200 ml of methylene chloride, 185 ml of water and 65 ml of a saturated aqueous solution of potassium carbonate. The organic phase is separated off and the aqueous phase is again extracted twice with 250-ml portions of methylene chloride. The organic phases are combined, washed with a salt-saturated aqueous solution and are dried over sodium sulphate. After filtration and evaporation, 7.87 g of an organic residue are obtained which, after crystallization from a mixture of hexane and ether, yield 4.8 g of product.

Yield: 63%
M.p.: 86°–87° C.
U.V. (MeOH)$\lambda_{max}$: 291, 284 nm.
M.S. m/e (%): 286 (M+ 47.5), 257 (49.5), 215 (20), 202 (31), 183 (14), 169 (8), 156 (45.5), 143 (11.5), 128 (13), 84 (100).
I.R. (CCl$_4$): 3450, 2960, 2820, 1731, 1465, 1439, 1166 cm$^{-1}$ (b) In accordance with the procedure described in example 1, the product is obtained in 62% yield.
M.p.: 106°–109° C.
U.V. (MeOH)$\lambda_{max}$: 225, 282, 290 nm
M.S. m/e (%): 258 (M+ 89), 229 (69); 186 (58); 174 (36); 157 (100), 144 (20); 129 (17); 115 (8); 84 (38).
I.R. (CHCl$_3$): 3625, 3474, 3023, 2970, 2840, 1520, 1465, 1340, 1230, 1049 cm$^{-1}$.
N.M.R. (CDCl$_3$)δ: 7.53–6.86 (m, 4H); 5.43 (bs, 1H); 3.76 (m, 2H); 3.23–2.20 (m, 9H), 1.90–1.23 (m, 2H); 0.93 (tr, 3H); 8.50 (bs, 1H).

EXAMPLE 5

1,2,3,4,5,6-hexahydro-3-benzyl-5-hydroxymethylazepino[4,5-b]indole (I: $R_1$=CH$_2$—C$_6$H$_5$; $R_2$, $R_3$, $R_4$=H; n=1)

A solution of 7 g (0.0324 mol) of 5-hydroxymethylazepino[4,5-b]indole, of 5.02 g (0.0388 mol) of diisopropylethylamine, and of 6.67 g (0.0388 mol) of benzyl bromide in 150 ml of chloroform is heated under reflux for 10 hours. The reaction mixture is then drowned in water and alkalified with a saturated aqueous solution of potassium carbonate. The organic phase is separated off and the aqueous phase is again extracted twice with 100 ml portions of chloroform. The organic phases are combined, washed with water, dried over magnesium sulphate, filtered and evaporated to dryness under vacuum. The residue, recrystallized from ether, yields 7.7 g of product.

Yield: 77.5%.
M.p.: 95° C.
N.M.R. (CDCl$_3$)δ: 8.30 (bs, 1H); 7.66–6.90 (m, 9H); 4.43 (bs, 1H); 3.93–3.50 (m, 4H); 3.33–2.26 (m, 7H).

EXAMPLE 6

1,2,3,4,5,6-hexahydro-3-methyl-5-benzoyloxymethylazepino[4,5-b]indole (I: $R_1$=CH$_3$; $R_2$=CO—C$_6$H$_5$; $R_3$, $R_4$=H; n=1)

3.27 g (0.023 mol) of benzoyl chloride in 50 ml of chloroform are added to a solution of 4.44 g (0.0193 mol) of 3-methyl-5-hydroxymethylazepino[4,5-b]indole and of 1.84 g (0.023 mol) of pyridine in 150 ml of chloroform. After being stirred overnight at ambient temperature, the reaction mixture is drowned in water and alkalified with a saturated aqueous solution of potassium carbonate. The organic phase is then treated as in example 5. The residue obtained is crystallized from ethanol and yields 4.1 g of product.

Yield: 63.6%
M.p.: 124° C.
U.V. (MeOH)$\lambda_{max}$: 227, 281, 292 nm
M.S. m/e (%): 334 (M+ 92), 291 (6); 278 (17); 213 (75); 197 (10), 178 (59); 170 (100); 156 (49); 104 (50).
I.R. (KBr): 3400, 2940, 2900, 2810, 1705, 1463, 1452, 1396, 1319, 1280, 1139 cm$^{-1}$.
N.M.R. (CDCl$_3$)δ: 8.23–7.76 (m, 3H); 7.63–6.90 (m, 7H), 4.83–4.46 (m, 2H), 3.58–2.20 (m, 10H), incl. 2.50 (s, 3H).

EXAMPLE 7

1,2,3,4,5,6-hexahydro-3-ethyl-5-benzoyloxymethylazepino[4,5-b]indole (I: $R_1$=C$_2$H$_5$; $R_2$=CO—C$_6$—H$_5$; $R_3$, $R_4$=H; n=1)

In accordance with the procedure described in example 6, 3-ethyl-5-hydroxymethylazepino[4,5-b]indole yields the product.
Yield: 75%
M.p.: 115°–117° C.
U.V. (MeOH)$\lambda_{max}$: 226, 281, 292 nm
M.S. m/e (%): 348 (M+ 27), 278 (8); 226 (31); 211 (6); 192 (30), 170 (100); 156 (47); 105 (59).
I.R. (KBr): 3385, 3060, 2980, 2830, 1752, 1455, 1393, 1327, 1280, 1130, 717 cm$^{-1}$.
N.M.R. (CDCl$_3$)δ: 8.10–7.66 (m, 3H), 7.50–6.80 (m, 7H), 4.76–4.46 (m, 2H); 3.46–2.43 (m, 9H), 1.10 (tr, 3H).

EXAMPLE 8

1,2,3,4,5,6-hexahydro-5-hydroxymethyl-6-methylazepino[4,5-b]indole (I: $R_1$, $R_2$, $R_4$=H; $R_3$=CH$_3$; N=1)

In accordance with the procedure described in example 1, 5-carbomethoxy-6-methylazepino[4,5-b]indole yields the product after reduction.
Yield: 78%.
M.p.: 124°–126° C.
U.V. (MeOH)$\lambda_{max}$: 226, 285, 292 nm
M.S. m/e (%): 230 (M+ 34), 212 (30), 200 (8); 188 (44); 170 (100); 144 (12); 128 (6); 115 (7); 91 (3).
I.R. (KBr): 3150, 2920, 1611, 1470, 1435, 1358, 1240, 1191, 1062, 745 cm$^{-1}$.
N.M.R. (CDCl$_3$)δ: 7.53–6.83 (m, 4H); 3.91 (dd, 2H); 3.58 (s, 3H), 3.51 (s, 2H); 3.45–2.56 (m, 7H).

EXAMPLE 9

1,2,3,4,5,6-hexahydro-3,6-dimethyl-5-hydroxymethylazepino[4,5-b]indole (I: $R_1$, $R_3$=CH$_3$; $R_2$, $R_4$=H, n=1)
(a)   1,2,3,4,5,6-hexahydro-3,5-dicarbomethoxy-6-methylazepino[4,5-b]indole   (IV: $R_1$=COOCH$_3$; $R_3$=CH$_3$; $R_4$=H).

In accordance with the procedure described in example 2(a), 12 g (0.045 mol) of 5-carbomethoxy-6-methylazepino[4,5-b]indole yield 12 g of product, after condensation with 5.52 g (0.0585 mol) of methyl chloroformate.
Yield: 84.4%
M.p.: 107°–110° C.
U.V. (MeOH)$\lambda_{max}$: 226, 286 nm M.S. m/e (%): 316 (M+ 89), 284 (100); 269 (30.7); 257 (72); 241 (25); 229 (60); 228 (87); 216 (56.7); 209 (15); 198 (42.5); 197 (54); 170 (75.7); 154 (23).

I.R. (KBr): 3460, 3000, 2950, 2900, 1780, 1700, 1690, 1470, 1440, 1410, 1400 cm$^{-1}$.

(b) In accordance with the procedure described in example 2b, 11 g (0.0348 mol) of the azepinoindole obtained in (a) are treated with 2.642 g (0.0696 mol) of lithium aluminium hydride and yield 9.5 g of organic material which, after crystallization from ethanol, yields 7.3 g of product.

Yield: 86%.
M.p.: 136° C.
U.V. (MeOH)$\lambda_{max}$: 228, 285, 293 nm
M.S. m/e (%): 244 (M+ 81), 214 (37); 200 (9); 186 (79); 171 (100) 158 (28); 144 (15); 122 (18); 115 (9); 74 (36); 58 (70).
I.R. (KBr): 3140, 2920, 2815, 1465, 1612, 1568, 1323, 1240, 1066, 1057, 985, 743 cm$^{-1}$.
N.M.R. (CDCl$_3$)δ: 7.56–6.90 (m, 4H); 5.15 (bs, 1H); 3.93 (dd, 2H) 3.56 (s, 3H); 3.23–2.83 (m, 5H), 2.58 (d, 1H), 2.43 (s, 3H); 2.26 (m, 1H).

EXAMPLE 10

1,2,3,4,5,6-hexahydro-3-ethyl-5-hydroxymethyl-6-methylazepino[4,5-b]indole (I: R$_1$=C$_2$H$_5$; R$_2$, R$_4$=H; R$_3$=CH$_3$; n=1)

(a) 1,2,3,4,5,6-hexahydro-3-acetyl-5-carbomethoxy-6-methylazepino[4,5-b]indole (IV: R$_1$=COCH$_3$; R$_3$=CH$_3$; R$_4$=H).

In accordance with the procedure described in example 3(a), 2.3 g of product are obtained from 2.58 g of 5-carbomethoxy-6-methylazepino[4,5-b]indole.

Yield: 76.6%
M.p.: 131°–132° C.
U.V. (MeOH)$\lambda_{max}$: 226, 286 nm
M.S. m/e (%): 300 (M+ 19.21); 268 (36.5); 257 (3.9); 241 (16.4); 228 (40); 225 (20); 216 (33); 209 (25); 184 (24); 170 (35); 157 (14); 41 (100).
I.R. (KBr): 3460, 3040, 3000, 2960, 1740, 1640, 1450, 1180 cm$^{-1}$.

(b) In accordance with the procedure described in example 2(b), 1 g of product is obtained from 2 g of the product described in (a).

Yield: 69.7%
M.p.: 70°–72° C.
U.V. (MeOH)$\lambda_{max}$: 228, 285, 292 nm
M.S. m/e (%): 258 (M+ 47); 228 (23); 212 (16); 188 (30); 186 (50); 184 (20); 171 (100); 158 (23); 144 (17); 129 (22); 88 (16); 72 (37); 41 (30).
I.R. (KBr): 3160, 3059, 2920, 2830, 1606, 1471, 1403, 1240, 1192, 1152, 1059, 951, 919, 738 cm$^{-1}$.
N.M.R. (CDCl$_3$)δ7.53–6.80 (m, 4H); 5.20 (bs, 1H); 4.23–3.76 (m, 2H); 3.53 (s, 3H); 3.33–2.30 (m, 9H) incl. 2.56 (q, 2H); 1.13 (tr, 3H).

EXAMPLE 11

1,2,3,4,5,6-hexahydro-3-methyl-5-hydroxymethyl-6-ethylazepino[4,5-b]indole (I: R$_1$=CH$_3$; R$_2$, R$_4$=H; R$_3$=C$_2$H$_5$; n=1)

In accordance with the procedure described in example 2, the product is obtained from 3,5-dicarbomethoxy-6-ethylazepino[4,5-b]indole.

M.p.: 129° C.
U.V. (MeOH)$\lambda_{max}$: 228, 285, 290 nm
M.S. m/e (%): 258 (56 M+); 200 (49); 185 (100); 184 (61); 129 (13); 74 (10); 58 (22).

I.R. (KBr): 3160, 2980, 2920, 2820, 1460, 1430, 1380, 1350, 1320, 1290, 1280, 1240 cm$^{-1}$.

EXAMPLE 12

1,2,3,4,5,6-hexahydro-3,6-diethyl-5-hydroxymethylazepino[4,5-b]indole (1: R$_1$, R$_3$=C$_2$H$_5$; R$_2$, R$_4$=H; n=1)

(a) 1,2,3,4,5,6-hexahydro-3-acetyl-5-carbomethoxy-6-ethylazepino[4,5-b]indole (IV: R$_1$=COCH$_3$; R$_3$=C$_2$H$_5$; R$_4$=H).

In accordance with the procedure described in example 3(a), 4.5 g of product are obtained from 7 g (0.0257 mol) of 5-carbomethoxy-6-ethylazepino[4,5]indole.

Yield: 56%
M.S. m/e (%): 314 (67 M+); 282 (93); 255 (27); 243 (36); 242 (100); 239 (36); 230 (63); 223 (28); 211 (20); 184 (46); 182 (30); 168 (23); 154 (21); 43 (30).

(b) In accordance with the procedure described in example 2(b), 2.1 g of product are obtained from 3 g of the product described in (a).

Yield: 81%
M.p.: 103° C.
U.V. (MeOH)$\lambda_{max}$: 229, 285, 293 nm
M.S. m/e (%): 272 (59 M+); 242 (14); 214 (10); 200 (71); 185 (100); 184 (77); 172 (16); 158 (13); 136 (16); 88 (21); 72 (53); 42 (29).
I.R. (KBr): 3180, 2980, 2840, 1470, 1370, 1350, 1330, 1270, 1230 cm$^{-1}$.

EXAMPLE 13:

1,2,3,4,5,6-hexahydro-3-dimethylaminoethyl-5-hydroxymethylazepino[4,5-b]indole (I: R$_1$

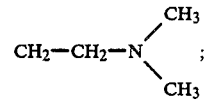

R$_2$, R$_3$, R$_4$=H; n=1)

A solution of 7 g (0.0324 mol) of 5-hydroxymethylazepino[4,5-b]indole, of 10.04 g (0.0777 mol) of diisopropylethylamine, and of 5.6 g (0.0388 mol) of 1-chloro-2-dimethylaminoethane hydrochloride in 150 ml of chloroform is heated under reflux for 15 hours. The reaction mixture is then drowned in water and alkalified with a saturated aqueous solution of potassium carbonate. The organic phase is separated off and the aqueous phase is again extracted twice with 100 ml portions of chloroform. The organic phases are combined, washed with water, dried over magnesium sulphate, filtered and evaporated to dryness under vacuum. The residue is crystallized from ethyl acetate and yields 8.1 g of product.

Yield: 87%
M.p.: 182°–184° C.
U.V. (MeOH)$_{max}$: 226, 282, 290 nm
M.S. m/e (%): 287 (8 M+); 257 (12); 230 (14); 229 (89); 199 (20); 186 (100); 170 (26); 168 (21); 156 (31); 144 (16); 101 (53); 58 (88).
I.R. (KBr): 3240, 3060, 2930, 2820, 1621, 1588, 1419, 1368, 1191, 1139, 1047, 917 cm$^{-1}$.
N.M.R. (CDCl$_3$+CD$_3$OD)δ: 2.30 (s, 6H); 3.06–1.41 (m, 8H); 4.16–3.05 (m, 5H); 7.53–6.80 (m, 4H).

EXAMPLE 14

1,2,3,4,5,6-hexahydro-3-diethylaminoethyl-5-hydroxymethylazepino[4,5-b]indole

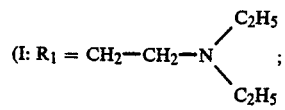

$R_2$, $R_3$, $R_4$=H; n=1)

(a) 1,2,3,4,5,6-hexahydro-3-diethylaminoacetyl-5-carbomethoxyazepino[4,5-b]indole (VI: R'=C$_2$H$_5$; R$_3$, R$_4$=H; m=1)

6 g (0.0245 mol) of 5-carbomethoxyazepino[4,5-b]indole are suspended in 350 ml of ethyl acetate. After adding 350 ml of 2M caustic soda, 3.25 g (0.0288 mol) of chloroacetyl chloride, dissolved in 30 ml of ethyl acetate, are added with intense stirring. After 10 minutes' stirring, the reaction is finished. The organic phase is separated off and the aqueous phase is extracted twice with 50-ml portions of ethyl acetate. The organic phases are combined, washed with water, dried over sodium sulphate and evaporated to dryness under vacuum. The residue is then taken up in 400 ml of tetrahydrofuran. 3.87 g (0.053 mol) of diethylamine are then added and stirring is continued for 12 hours at ambient temperature. When the reaction is complete, the reaction medium is evaporated to dryness under vacuum and the residue is dissolved in 150 ml of methylene chloride. The methylene chloride is then washed with water, dried over sodium sulphate and evaporated to dryness under vacuum. The residue is dissolved in acetone and isolated in the form of a hydrochloride.

Weight: 7.3 g. Yield: 75.5%

U.V. (MeOH)λ$_{max}$: 222, 289, 292 nm

M.S. m/e (%): 357 (51 M+); 214 (5); 169 (12); 143 (7); 86 (100);

I.R. (KBr): 3200, 2968, 2840, 1730, 1630, 1460 cm$^{-1}$.

N.M.R. (CDCl$_3$)δ: 7.53–6.76 (m, 4H); 4.46–3.50 (m, 8H) incl. 3.70 (s, 2H) and 3.63 (s, 3H), 3.43–2.83 (m, 4H); 2.46 (q, 4H); 0.96 (tr. 6H).

(b) A solution of 4 g (0.0112 mol) of the product prepared in (a), dissolved in 100 ml of tetrahydrofuran, is added dropwise under argon to a suspension of 1.3 g (0.0343 mol) of lithium aluminium hydride in 100 ml of anhydrous tetrahydrofuran. A treatment similar to that described in example 1 makes it possible to isolate 3.1 g of product, after crystallization from acetonitrile.

Yield: 88%

M.p.: 163° C.

U.V. (MeOH)λ$_{max}$: 225, 282, 290 nm

M.S. m/e (%): 315 (0.3 M+); 229 (2); 156 (2); 100 (3); 86 (100); 72 (8); 70 (3); 58 (32); 54 (10); 44 (11); 42 (16).

I.R. (KBr): 3230, 3060, 2980, 2880, 2820, 1620, 1589, 1469, 1373, 1196, 1139, 1042, 919, 731 cm$^{-1}$.

N.M.R. (CDCl$_3$+CD$_3$OD)δ: 7.45–6.80 (m, 4H); 4 (dd, 1H); 3.60 (dd, 1H), 3.40–3.08 (m, 2H); 3.06–2.26 (m, 10H), incl. 2.56 (q, 4H); 1.06 (tr, 6H).

EXAMPLE 15

1,2,3,4,5,6-hexahydro-3-morpholinoethyl-5-hydroxymethylazepino[4,5-b]indole (I: R$_1$=

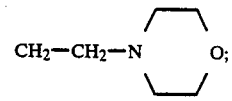

$R_2$, $R_3$, $R_4$=H; n=1)

(a) 1,2,3,4,5,6-hexahydro-3-morpholinoacetyl-5-carbomethoxyazepino[4,5-b]indole (VI:

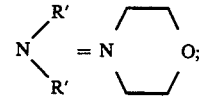

R$_3$, R$_4$=H; m=1

Using the procedure described in example 14(a), the product is obtained in the form of a hydrochloride.

U.V. (MeOH)λ$_{max}$: 223, 284, 292 nm

M.S. m/e (%): 371 (35 M+); 313 (3); 227 (11); 214 (7); 183 (5); 169 (10); 156 (10); 100 (100).

I.R. (KBr): 3260, 2950; 2860, 1730, 1635, 1460, 1115, 1012 cm$^{-1}$.

N.M.R. (CDCl$_3$)δ: 8.93 (m, 1H); 7.53–6.83 (m, 4H); 4.26–3.96 (m, 3H); 3.96–3.53 (m. 9H) incl. 3.61 (s, 3H); 3.32–2.83 (m, 4H) incl. 3.15 (s, 2H); 2.60–2.20 (m, 4H).

(b) 1,2,3,4,5,6-hexahydro-3-morpholinoacetamido-5-carbomethoxyazepino[4,5-b]indole (VIL:

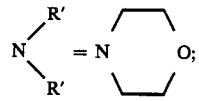

R$_3$, R$_4$=H; m=1)

A solution of 6 g (0.0245 mol) of 5-carbomethoxyazepino[4,5-b]indole, of 3.81 (0.0295 mol) of diisopropylethylamine, and of 4.82 g (0.0295 mol) of chloroacetylmorpholine in 150 ml of chloroform is heated under reflux for 5 hours. The reaction mixture is then treated as in example 5, to yield 7.1 g of product.

Yield: 77.8%

The product is crystallized in the form of a methanesulphonate.

U.V. (MeOH)λ$_{max}$: 225, 284, 292 nm

I.R. (KBr): 3271, 2963; 2900, 2858, 1723, 1630, 1463, 1441, 1274, 1120 cm$^{-1}$.

N.M.R. (CDCl$_3$)δ: 8.40 (bs, 1H); 7.56–6.93 (m, 4H); 3.96 (dd, 1H); 3.66 (s, 3H); 3.63 (m, 8H); 3.48 (s, 2H); 3.36 (d, 1H), 3.16 (d, 1H); 2.93 (m, 4H).

(c) The lithium aluminium hydride reduction of the products described in (a) and in (b), in accordance with the procedure described in example 1, enables the product to be obtained.

M.p. 268° C.

U.V. (MeOH)λ$_{max}$: 226, 283, 291 nm

I.R. (KBr): 3250, 2900; 2800, 1468, 1359, 1310, 1150, 1114, 1043, 928 cm$^{-1}$.

N.M.R. (CDCl$_3$)δ: 8.80 (m, 1H); 7.56–6.73 (m, 4H); 4.16 (m, 1H); 4.00–3.23 (m, 7H); 3.23–2.00 (m, 14H).

EXAMPLE 16

1,2,3,4,5,6-hexahydro-3-piperidinoethyl-5-hydroxymethylazepino[4,5-b]indole (I: R$_1$=

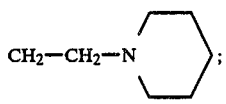

$R_2, R_3, R_4=H; n=1)$ (a) 1,2,3,4,5,6-hexahydro-3-piperidinoacetyl-5-carbomethoxyazepino[4,5-b]indole (VI:

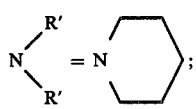

$R_3, R_4=H; m=1)$

Using the procedure described in example 14(a), the product is obtained in base form.

M.p.: 149° C.
U.V. (MeOH)λ$_{max}$: 223, 284, 292 nm
M.S. m/e (%): 369 (32 M+); 310 (1.2); 227 (1.94); 214 (2.46); 183 (2.29); 169 (3.62); 155 (5.23); 98 (100); 84 (14).
I.R. (KBr): 3280, 2940, 1740, 1630, 1460, 1460, 1450, 1430, 1380, 1310 cm$^{-1}$.

(b) The reduction of the product described in (a) in accordance with the procedure described in example 1 enables the product to be obtained.

M.p.: 174° C.
U.V. (MeOH)λ$_{max}$: 226, 282, 290 nm
M.S. m/e (%): 327 (1 M+); 229 (6); 186 (8); 170 (4); 156 (7); 141 (22); 129 (13); 98 (100); 86 (17); 70 (7); 58 (10); 55 (14).
I.R. (CHCl$_3$): 2950, 2825, 1458, 1481, 1355, 1339, 1312, 1143, 1111, 1038, 977, 924 cm$^{-1}$.
N.M.R. (CDCl$_3$)δ: 9.00 (bs, 1H); 7.56-6.76 (M, 4H); 4.03 (m, 1H); 3.80-3.26 (m, 2H); 3.13-1.93 (m, 15H), 1.90-1.20 (m, 6H)

EXAMPLE 17

1,2,3,4,5,6-hexahydro-3-pyrrolidinoethyl-5-hydroxymethylazepino[4,5-b]indole (I: R$_1$=

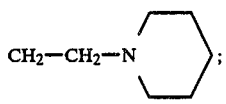

$R_2, R_3, R_4=H; n=1).$ (a) 1,2,3,4,5,6-hexahydro-3-pyrrolidinoacetyl-5-carbomethoxyazepino[4,5-b]indole (VI:

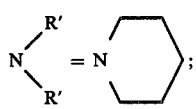

$R_3, R_4=H; m=1)$

Using the procedure described in example 14a), the product is obtained in base form.

M.p.: 166° C.
U.V. (MeOH)λ$_{max}$: 283, 292 nm.
M.S. m/e (%): 355 (22 M+); 183 (3); 129 (3); 85 (16); 84 (100); 82 (4); 55 (15); 42 (34).

I.R. (KBr): 3400, 3340, 2960, 2900, 1735, 1650, 1620, 1610, 1460, 1430, 1380 cm$^{-1}$.

(b) 1,2,3,4,5,6-hexahydro-3-pyrrolidinoacetamido-5-carbomethoxyazepino[4,5-b]indole (VII:

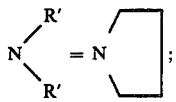

$R_3, R_4=H; m=1)$

Using the procedure described in example 15(b) the product is obtained in base form.

M.p.: 166°-168.5° C.
U.V. (MeOH)λ$_{max}$: 225, 285, 292 nm
M.S. m/e (%): 355 (34 M+); 343 (8); 324 (3); 296 (2); 257 (52); 227 (20); 215 (58); 197 (14); 183 (10); 168 (13); 156 (30); 141 (100)
I.R. (KBr): 3250, 2957, 2887, 1732, 1630, 1462, 1340, 1320, 1232, 1201, 911 cm$^{-1}$.
N.M.R. (CDCl$_3$)δ: 8.6 (M, 1H); 7.56-6.80 (m, 4H); 3.93 (dd, 1H); 3.66 (s, 3H); 3.60-3.16 (m, 8H); 2.93 (m, 4H); 1.86 (m, 4H).

(c) Lithium aluminium hydride reduction of the products described in (a) and (b) in accordance with the procedure described in example 1 enables the product to be obtained.

M.p.: 178.2° C.
U.V. (MeOH)λ$_{max}$: 226, 284, 291 nm
M.S. m/e (%): 313 (5 M+); 283 (10); 289 (73); 199 (7); 186 (40); 170 (10); 156 (11); 127 (46); 115 (18); 84 (100).

EXAMPLE 18

1,2,3,4,5,6-hexahydro-3-dimethylaminoethyl-5-hydroxymethyl-6-methylazepino[4,5-b]indole (I: R$_1$=

$$CH_2-CH_2-N\begin{array}{c}CH_3\\CH_3\end{array};$$

$R_2, R_4=H; R_3=CH_3; n=1)$

A solution of 5 g (0.0217 mol) of 5-hydroxymethyl-6-methylazepino[4,5-b]indole, of 6.74 g (0.0521 mol) of diisopropylethylamine, and of 3.756 g (0.0260 mol) of 1-chloro-2-dimethylaminoethane hydrochloride in 150 ml of chloroform is heated under reflux for 20 hours. The reaction mixture is then treated as in example 5. The residue is taken up in acetonitrile and, after crystallization, yields 5.6 g of product.

Yield: 85.4%
M.p.: 141° C.
U.V. (MeOH)λ$_{max}$: 228, 285, 294 nm
M.S. m/e (%): 301 (12 M+).
I.R. KBr): 3060, 2930, 2820, 1606, 1561, 1473, 1387, 1320, 1259, 1149, 1137, 1013, 1007, 742 cm$^{-1}$.
N.M.R. (CDCl$_3$)δ: 7.50-6.76 (m, 4H); 3.90 (m, 1H); 3.60 (s, 3H); 3.66-1.96 (m, 16H); 2.30 (s, 3H).

EXAMPLE 19

1,2,3,4,5,6-hexahydro-3-pyrrolidinoethyl-5-hydroxymethyl-6-methylazepino[4,5-b]indole (I: R$_1$

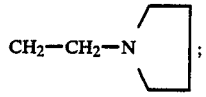

R$_2$, R$_4$=H; R$_3$=CH$_3$; n=1)

In accordance with the procedure described in example 18, the condensation of 1-chloro-2-pyrrolidinoethane hydrochloride with 5-hydroxymethyl-6-methylazepino[4,5-b]indole yields the product.

M.p. 117° C.

U.V. (MeOH)λ$_{max}$: 227, 285, 293 nm

M.S. m/e (%): 327 (1 M+); 297 (35); 243 (100); 213 (11); 200 (50); 183 (24); 182 (23); 170 (18); 127 (46); 84 (93); 42 (17)

I.R. (KBr): 3180, 2990, 2800, 1470, 1450, 1370, 1350, 1330, 1240, 1190, 1140, 1120, 1060, 1050 cm$^{-1}$.

Example 20

1,2,3,4,5,6-hexahydro-3-diethylaminoethyl-5-hydroxymethyl-6-methylazepino[4,5-b]indole (I: R$_1$=

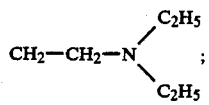

R$_2$, R$_4$=H; R$_3$=CH$_3$; n=1)

In accordance with the procedure described in example 18, the condensation of 1-chloro-2-diethylaminoethane hydrochloride with 5-hydroxymethyl-6-methylazepino[4,5-b]indole yields the product.

M.p.: 97°-98° C.

U.V. (MeOH)λ$_{max}$: 228, 285 nm

M.S. m/e (%): 329 (4 M+); 300 (26); 299 (81); 244 (49); 243 (100); 213 (13); 200 (83); 184 (35); 183 (27); 170 (35); 129 (39); 86 (93)

I.R. (KBr): 3140, 2960, 2840, 1460, 1360, 1320, 1270, 1250, 1240, 1190, 1140, 1050, 1000 cm$^{-1}$.

EXAMPLE 21

1,2,3,4,5,6-hexahydro-3-morpholinoethyl-5-hydroxymethyl-6-methylazepino[4,5-b]indole (I: R$_1$

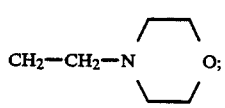

R$_2$, R$_4$=H; R$_3$=CH$_3$; n=1)

In accordance with the procedure described in example 18, the condensation of 1-chloro-2-morpholinoethane hydrochloride with 5-hydroxymethyl-6-methylazepino[4,5-b]-indole yields the product.

M.p.: 120° C.

U.V. (MeOH)λ$_{max}$: 228, 285, 292 nm

M.S. m/e (%): 343 (2M$^{30}$); 313 (34); 244 (100); 200 (67); 184 (30); 170 (26); 158 (10); 143 (23); 100 (26).

I.R. (KBr): 3220, 2960, 2940, 2900, 1470, 1390, 1370, 1350, 1320, 1300, 1280, 1250, 1190, 1150, 1120, 1050, 1030 cm$^-$.

EXAMPLE 22:

1,2,3,4,5,6-hexahydro-3-ethyl-5-hydoxyethylazepino[4,5-b]indole (I: R$_1$=C$_2$H$_5$; R$_2$, R$_3$, R$_4$=H; n=2)

(a) 1,2,3,6-tetrahydro-3-ethyl-5-carbomethoxymethylazepino[4,5-b]indol-4-one.

15 g of 1-carbomethoxymethyl-1'-carbomethoxy-2-ethyl-1,2,3,4-tetrahydro-β-carboline, dissolved in 225 ml of toluene, and 45 ml of acetic acid are heated under reflux for 10 hours. The reaction mixture is then alkalified with a 2M caustic soda solution to pH 9. The organic phase is separated off, and the aqueous phase is again extracted twice with 150-ml portions of toluene. The organic phases are combined, washed with water to neutrality, dried over magnesium sulphate and evaporated to dryness under vacuum. 8 g of residue are obtained. The residue is dissolved in 150 ml of glacial acetic acid and is hydrogenated at atmospheric pressure in the presence of 1 g of charcoal containing 20% palladium. After 24 hours, the reaction is complete. The catalysts is filtered off and the acetic solution is alkalified to pH 9 with a 2M aqueous solution of caustic soda. The alkaline aqueous phase is extracted three times with 150-ml portions of methylene chloride. The combined organic phases are washed with water to neutrality, are dried over magnesium sulphate and are evaporated to dryness. The residue is recrystallized from methanol and yields 10.8 g of product.

Yield: 79%

M.p.: 153° C.

U.V. (MeOH)λ$_{max}$: 222, 283, 290 nm

M.S. m/e (%): 300 (100M+); 269 (41); 268 (70); 241 (56); 240 (82); 170 (87); 1689 (33); 156 (89); 155 (44); 129 (25).

I.R. (KBr): 3300, 2990, 1740, 1640, 1490, 1450, 1380, 1360, 1330, 1290, 1260, 1200, 1020 cm$^{-1}$.

(b) 10 g of the product prepared in (a), dissolved in 100 ml of tetrahydrofuran, are added dropwise under argon to a suspension of 2.53 g of lithium aluminium hydride in 100 ml of tetrahydrofuran. The reaction medium is then treated as in example 1 and 7.1 g of product are obtained.

Yield: 82%

M.p.: 152° C.

U.V. (MeOH)λ$_{max}$: 224, 281, 289 nm

M.S. m/e (%): 258 (97M+); 227 (15); 201 (37); 188 (85); 170 (83); 168 (36); 156 (100); 154 (31); 144 (30); 128 (24); 72 (63); 43 (45).

I.R. (KBr): 3200, 2980, 2920, 2840, 2680, 1460, 1450, 1380, 1350, 1340, 1200, 1140, 1070, 1020, 1010 cm$^{-1}$.

The compounds of the invention have been the subject of a pharmacological study.

1. Toxicity

The 50% lethal dose (LD$_{50}$) of the compounds is determined in CD1 strain mice by a graphical method. The LD$_{50}$ ranges from 40 to 2,000 mg/kg orally. It has been calculated according to Lichtfield and Wilcoxon's (1970) standard method.

2. Hypobaric hypoxia

CD1 strain mice are kept in an atmosphere depleted in oxygen by producing a partial vacuum (190 mm of mercury, corresponding 5.25% of oxygen).

The animals' survival time is noted. This time is increased by agents capable of promoting tissue, and especially cerebral, oxygenation.

The compounds under study are administered orally, in several doses, 30 minutes before the test.

The results are expressed in percentage increase in survival time relative to untreated animals.

By plotting the percentage of survival of the treated animals relative to the controls, as a function of the logarithm of the product dose which is administered, it is possible to determine the "$ED_{50}$" (effective dose), that is to say the dose, expressed in mg/kg, giving rise to 50% activity in the test. The $ED_{50}$ varies from 1.9 to 200 mg/kg orally, approximately.

In order to assess the therapeutic action of a product, the value of the $ED_{50}$ of the product is compared to the $LD_{50}$ for the same product, and this enables a therapeutic index (T.I.) to be defined. TI=$LD_{50}$ mg/kg/$ED_{50}$ mg/kg. The therapeutic index varies from 9 to 126.

3. Histotoxic hypoxia

NMRI strain mice are injected intravenously with potassium cyanide (KCN) at a dosage of 2.5 mg/kg.

On average, 80% of the controls die within 2 minutes.

The percentage of survival obtained after 30 minutes is noted in each series.

The compounds under study are administered orally, in various doses, 30 minutes before the injection of KCN.

The results are expressed as percentage of survival for each series.

Agents which are capable of promoting tissue, and especially cerebral, oxygenation lead to survival of the animals and hence exert a protective action in this case of hypoxia.

By plotting the percentage of survival in the treated animals relative to the controls, as a function of the logarithm of the product dose administered, it is possible to determine the "$ED_{50}$" (effective dose): see section 2.

The $ED_{50}$ of the compounds in this test lies generally between 5° and 10° of their $LD_{50}$.

The therapeutic index, as defined in section 2 above, therefore varies from 5 to 10.

4. Normobaric hypoxic hypoxia

NMRI strain mice are maintained in an enclosure through which a stream of nitrogen at a controlled flow is passed for approximately 25 seconds; then, air is reintroduced into the enclosure by passing compressed air through at a controlled flowrate for approximately 30 seconds. The enclosure is then opened and the mice are gently placed in a cage. The percentage survival after 30 min. is noted for each series. A proportion of 90 to 100% of the controls die under these conditions. Agents capable of promoting tissue, and especially cerebral, oxygenation produce survival of the animals and thus exert a protective action in this case of hypoxia.

The compounds under study are administered orally, in several doses, 30 minutes before the test.

The animals treated with the compounds under study exhibit a high proportion of survival.

By plotting the percentage survival of the treated animals relative to the controls, as a function of the logarithm of the product dose administered, it is possible to determine the "$ED_{50}$": see section 2. The $ED_{50}$ varies from 6.8 to 92 mg/kg. The therapeutic index, as defned in section 2 above, varies from 15 to 80.

We claim:

1. A 1,2,3,4,5,6-hexahydro-5-hydroxyalkylazepino[4,5-b]-indole of the formula:

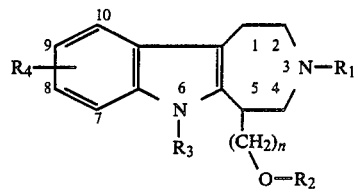

in which $R_1$ denotes a hydrogen atom, a lower alkyl radical having from 1 to 5 carbon atoms, a lower akenyl radical having from 1 to 5 carbon atoms, benzyl radical, an alkylamino radical of the formula

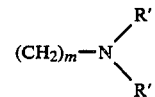

where the groups R' are either hydrogen atoms or lower alkyl radicals having from 1 to 5 carbon atoms of form, together with the nitrogen atom to which they are attached, a heterocyclic nucleus of the morpholinyl, piperidinyl, pyrrolidinyl or piperazinyl type, and m is 2 or 3, $R_2$ denotes a hydrogen atom or acyl radical of from 1 to 7 carbon atoms, $R_3$ denotes a hydrogen atom or a lower alkyl having from 1 to 2 carbon atoms or benzyl radical, $R_4$ denotes a hydrogen or halogen atom, a lower alkyl radical having from 1 to 5 carbon atoms, a lower alkoxy radical having from 1 to 5 carbon atoms or a trifluoromethyl radical, and n is 1 or 2, and pharmaceutically acceptable acid addition salts.

2. The compounds of claim 1, selected from the group comprising:

1,2,3,4,5,6-hexahdydro-5-hydroxymethylazepino[4,5-b]indole;

1,2,3,4,5,6-hexahydro-3-methyl-5-hydroxymethylazepino[4,5-b]indole;

1,2,3,4,5,6-hexahydro-3-ethyl-5-hydroxymethylazepino[4,5-b]indole;

1,2,3,4,5,6-hexahydro-3-propyl-5-hydroxymethylazepino-[4,5-b]indole;

1,2,3,4,5,6-hexahydro-5-hydroxymethyl-6-methylazepino[4,5-b]indole;

1,2,3,4,5,6-hexahydro-3,6-dimethyl-5-hydroxymethylazepino[4,5-b]indole;

1,2,3,4,5,6-hexahydro-3-ethyl-5-hydroxymethyl-6-methylazepino[4,5-b]indole;

1,2,3,4,5,6-hexahydro-3-methyl-5-hydroxymethyl-6-ethylazepino[4,5-]indole; and 1,2,3,4,5,6-hexahydro-3-ethyl-5-hydroxymethylazepino[4,5-b]indole.

3. A process for the preparation of a 1,2,3,4,5,6-hexahydro-5-hydroxalkylazepino[4,5-b]-indole of formula:

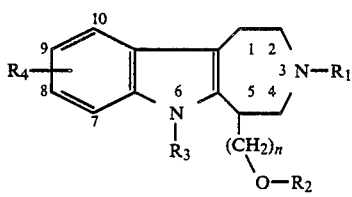

in which
R₁ denotes a hydrogen atom, a lower alkyl radical having from 1 to 5 carbon atoms, a lower alkenyl radical having from 1 to 5 carbon atoms, a benzyl radical, an alkylamino radical of the formula

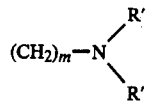

where the groups R' are either hydrogen atoms or lower alkyl radicals having from 1 to 5 carbon atoms or form, together with the nitrogen atom to which they are attached, a heterocyclic nucleus of the morpholinyl, piperidinyl, pyrrolidinyl or piperazinyl type, and m is 2 or 3;
R₂ denotes a hydrogen atom or acyl radical of from 1 to 7 carbon atoms;
R₃ denotes a hydrogen atom or a lower alkyl having from 1 to 2 carbon atoms or benzyl radical;
R₄ denotes a hydrogen or halogen atom, a lower alkyl radical having from 1 to 5 carbon atoms, a lower alkoxy radical having from 1 to 5 carbon atoms or a trifluoromethyl radical; and n is 1 or 2, and pharmaceutically acceptable acid addition salts wherein n=1 including the steps of:
reduction of the carbo alkoxy group of a corresponding 1,2,3,4,5,6-hexahydro-5carbo alkoxy azepino[4,5-b]indole of formula:

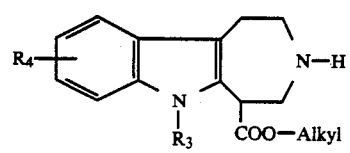

in which
R₃ denotes a hydrogen atom or a lower alkyl having from 1 to 2 carbon atoms or benzyl radical;
R₄ denotes a hydrogen or halogen atom, a lower alkyl radical having from 1 to 5 carbon atoms, a lower alkoxy radical having from 1 to 5 carbon atoms or a trifluoromethyl radical;
substitution of the nitrogen in position 3 by R₁ where
R₁ denotes a hydrogen atom, a lower alkyl radical having from 1 to 5 carbon atoms, a lower alkenyl radical having from 1 to 5 carbon atoms, a benzyl radical, an alkylamino radical of the formula

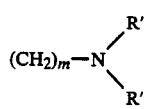

where the groups R' are either hydrogen atoms or lower alkyl radicals having from 1 to 5 carbon atoms or form, together with the nitrogen atom to which they are attached, a heterocyclic nucleus of the morpholinyl, piperidinyl, pyrrolidinyl or piperazinyl type, and m is 2 or 3; and, if appropriate;
substitution of R₂ for the oxygen atom resulting from the reduction of the carbon alkoxy group where
R₂ denotes a hydrogen atom or acyl radical of from 1 to 7 carbon atoms.
4. The process according to claim 3, wherein the substitution of the nitrogen is effected by the condensation of a lower alkyl having from 1 to 5 carbon atoms, a benzyl or an alkylamino halide of the formula X—(CH₂)ₘ—NR'R' where x denotes a halogen atom and m=1 or 2, in the presence of a tertiary amine in a chlorinated aliphatic hydrocarbon, at a temperature of between 20° C. and the reflux temperature of the solvent.

5. A process for the preparation of; a 1,2,3,4,5,6-hexahydro-5-hydroxalkylazepino indole of formula:

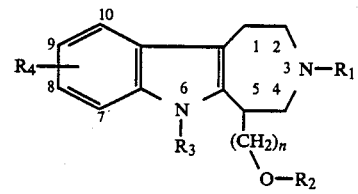

in which
R₁ denotes a hydrogen atom, a lower alkyl radical having from 1 to 5 carbon atoms, a lower alkenyl radical having from 1 to 5 carbon atoms, a benzyl radical, an alkylamino radical of the formula

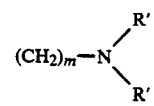

where the groups R' are either hydrogen atoms or alkyl radicals or form, together with the nitrogen atom to which they are attached, a heterocyclic nucleus of the morpholinyl, piperidinyl, pyrrolidinyl or piperazinyl type, and m is 2 or 3;
R₂ denotes a hydrogen atom or acyl radical of 1 to 7 carbon atoms;
R₃ denotes a hydrogen atom or a lower alkyl having from 1 to 2 carbon atoms or benzyl radical;
R₄ denotes a hydrogen or halogen atom, a lower alkyl radical having from 1 to 5 carbon atoms, a lower alkoxy radical having from 1 to 5 carbon atoms or a trifluoromethyl radical; and n is 1 or 2, and pharmaceutically acceptable acid addition salts wherein n=1, including the steps of:
substitution by R₁ where
R₁ denotes a hydrogen atom, a lower alkyl radical having from 1 to 5 carbon atoms, a lower alkenyl radical having from 1 to 5 carbon atoms, a benzyl radical, an alkylamino radical of the formula

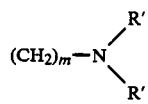

where the groups R' are either hydrogen atoms or alkyl radicals or form, together with the nitrogen atom to which they are attached, a heterocyclic nucleus of the morpholinyl, piperidinyl, pyrrolidinyl or piperazinyl type, and m is 2 or 3; of the nitrogen in position 3 of the compound of the formula

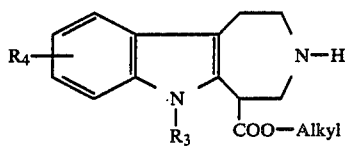

in which
R$_3$ denotes a hydrogen atom or a lower alkyl having from 1 to 2 carbon atoms or benzyl radical;
R$_4$ denotes a hydrogen or halogen atom, a lower alkyl radical having from 1 to 5 carbon atoms, a lower alkoxy radical having from 1 to 5 carbon atoms or a trifluoromethyl radical;
reduction of the carbo alkoxy group; and, if appropriate, substitution by R$_2$ for the oxygen atom resulting from the reduction of the carbomethoxy group, where R$_2$ denotes a hydrogen atom or acyl radical of from 1 to 7 carbon atoms.

6. The process of claim 5 wherein the reduction of the carbomethoxy group in position 5 is effected in an inert organic solvent at a temperature between 20° C. and the reflux temperature of the solvent, in the presence of a reducing agent.

7. The process of claim 5 wheren the substitution by R$_2$ of the oxygen of the —OH group resulting from the reduction of the carbomethoxy group in position 5 is effected by condensation of benzoylchloride in the presence of pyridine in a chlorinated aliphatic hydrocarbon at normal temperature.

8. The process of claim 7 wherein:
said chlorinated aliphatic hydrocarbon is selected from the group of chloroform and dichloroethane.

9. The process of claim 5, wherein the substitution of the nitrogen in position 3 is effected by the condensation of an aliphatic or aromatic aldehyde with the starting compound IIa to form methanoazepino-indoles of formula

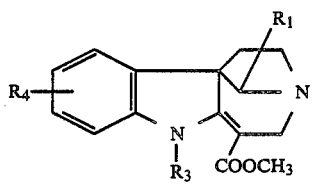

wherein
R$_1$ denotes a hydrogen atom, a lower alkyl radical having from 1 to 5 carbon atoms, a lower alkenyl radical having from 1 to 5 carbon atoms, a benzyl radical, an alkylamino radical of the formula

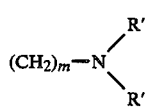

where the groups R' are either hydrogen atoms or alkyl radicals or form, together with the nitrogen atom to which they are attached, a heterocyclic nucleus of the morpholinyl, piperidinyl, pyrrolidinyl or piperazinyl type, and m is 2 or 3;
R$_3$ denotes a hydrogen atom or a lower alkyl having from 1 to 2 carbon atoms or benzyl radical;
R$_4$ denotes a hydrogen or halogen atom, a lower alkyl radical having from 1 to 5 carbon atoms, alkoxy radical having from 1 to 5 carbon atoms or a trifluoromethyl radical; and
by reduction of the compound of formula III in an organic solvent such as methanol or ethanol, at normal temperature, in the presence of sodium cyanoborohydride.

10. The process of claim 5 wherein the substitution of the nitrogen in position 3 is effected by condensation of a lower alkyl having from 1 to 5 carbon atoms, a lower alkenyl having from 1 to 5 carbon atoms or benzyl halide with the compound IIa, in the presence of a tertiary amine, in a chlorinated aliphatic hydrocarbon.

11. The process of claim 5 wherein the substitution of the nitrogen in position 3 is effected by condensation on a lower alkyl having from 1 to 5 carbon atoms, chloroformate or an acid chloride, in a binary system consisting of a solution of compound IIa in ethyl acetate and an aqueous solution of caustic soda.

12. The process of claim 5 wherein the substitution of the nitrogen in position 3 by a radical R$_1$ corresponding to an alkylamino group is effected by addition of an acid chloride of the formula X—(CH$_2$)m—COCL where X denotes a halogen atom and m=1 or 2, to a binary system consisting of a solution of compound IIa in ethyl acetate and an aqueous solution of caustic soda, in order to obtain an intermediate product of formula

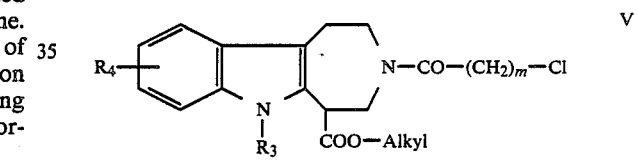

and by condensation of compound V with primary or secondary amines in an organic solvent.

13. The process of claim 5 wherein the substitution of the nitrogen in position 3 by a radical R$_1$ corresponding to an alkylamino group is effected by bringing compound IIa into contact with haloamides of the type

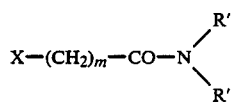

or alkylamine halides of the type

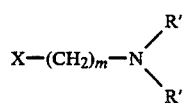

in which X denotes a halogen atom and m denotes an integer ranging from 1 to 3, in the presence of a tertiary amine, in a chlorinated aliphatic hydrocarbon, or in the presence of potassium carbonate in methyl ethyl ketone.

14. A process for the preparation of 1,2,3,4,5,6-hexahydro-5-hydroxalkylazepino[4,5-b]-indole of formula:

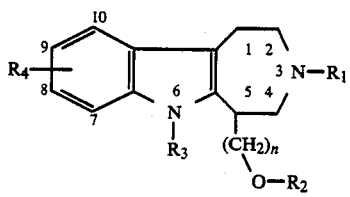

I in which
R₁ denotes a hydrogen atom, a lower alkyl radical having from 1 to 5 carbon atoms, a lower alkenyl radical having from 1 to 5 carbon atoms, a benzyl radical, an alkylamino radical of the formula

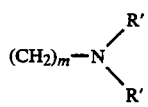

where the groups R' are either hydrogen atoms or alkyl radicals or form, together with the nitrogen atom to which they are attached, a heterocyclic nucleus of the morpholinyl, piperidinyl, pyrrolidinyl or piperazinyl type, and m is 2 or 3;
R₂ denotes a hydrogen atom or acyl radical of from 1 to 7 carbon atoms;
R₃ denotes a hydrogen atom or a lower alkyl having from 1 to 2 carbon atoms or benzyl radical;
R₄ denotes a hydrogen or halogen atom, a lower alkyl radical having from 1 to 5 carbon atoms, a lower alkoxy radical having from 1 to 5 carbon atoms or a trifluoromethyl radical; and n is 1 or 2, and pharmaceutically acceptable acid addition salts wherein n=2 including the steps of:
catalytic reduction of the carboxymethylene group in the compound corresponding to the formula

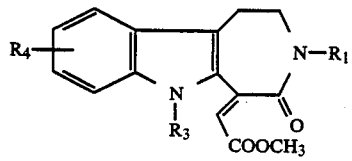

IIb wherein
R₁ denotes a hydrogen atom, a lower alkyl radical having from 1 to 5 carbon atoms, a lower alkenyl radical having from 1 to 5 carbon atoms, a benzyl radical, an alkylamino radical of the formula

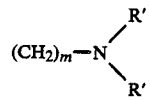

where the groups R' are either hydrogen atoms or alkyl radicals or form, together with the nitrogen atom to which they are attached, a heterocyclic nucleus of the morpholinyl, piperidinyl, pyrrolidinyl or piperazinyl type, and m is 2 or 3;
R₃ denotes a hydrogen atom or a lower alkyl having from 1 to 2 carbon atoms or benzyl radical;
R₄ denotes a hydrogen or halogen atom, a lower alkyl radical having from 1 to 5 carbon atoms, a lower alkoxy radical having from 1 to 5 carbon atoms or a trifluoromethyl radical in order to obtain the intermediate compound of formula

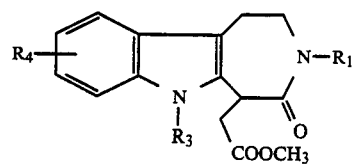

IX reduction of the carbomethoxy group; and, if appropriate, substitution by R₂ for the oxygen atom in position 5 resulting from the reduction of the carbomethoxy group where
R₂ denotes a hydrogen atom or acyl radical of from 1 to 7 carbon atoms.

15. The process of claim 14 wherein the catalytic reduction of the carboxymethylene is by means of palladium-containing charcoal, in a suitable solvent at temperatures of between 20° C. and 40° C.

16. The process of claim 11 wherein the reduction of the carbomethoxy group in position 5 is effected in an inert organic solvent, at a temperature between 20° C. and the reflux temperature of the solvent, in the presence of a reducing agent.

17. The process of claim 11 wherein the substitution by R₂ of the oxygen resulting from the reduction of the carbomethoxy group in position 5 is effected by condensation of benzoylchloride in the presence of pyridine in a chlorinated aliphatic hydrocarbon at normal temperature.

18. The process of claim 17 wherein:
said chlorinated aliphatic hydrocarbon is selected from the group of chloroform and dichloroethane.

19. The compound of formula

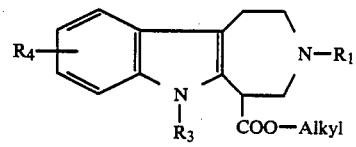

wherein
R₁ denotes a hydrogen atom, a lower alkyl radical having from 1 to 5 carbon atoms, a lower alkenyl radical having from 1 to 5 carbon atoms a benzyl radical, an alkylamino radical of the formula

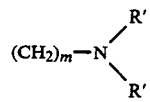

where the groups R' are either hydrogen atoms or alkyl radicals or form, together with the nitrogen atom to which they are attached, a heterocyclic nucleus of the morpholinyl, piperidinyl, pyrrolidinyl or piperazinyl type, and m is 2 or 3;
R₃ denotes a hydrogen atom or a lower alkyl having from 1 to 2 carbon atoms or benzyl radical;
R₄ denotes a hydrogen or halogen atom, a lower alkyl radical having from 1 to 5 carbon atoms, a lower alkoxy radical having from 1 to 5 carbon atoms or a trifluoromethyl radical; and pharmaceutically acceptable acid addition salts.

20. The compound of formula

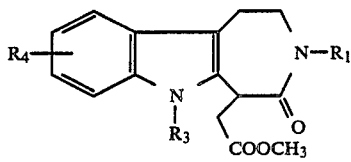

IX

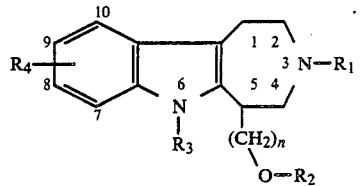

I wherein $R_1$ denotes a hydrogen atom, a lower alkyl radical having from 1 to 5 carbon atoms, a lower alkenyl radical having from 1 to 5 carbon atoms, a benzyl radical, an alkylamino radical of the formula

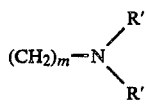

where the groups R' are either hydrogen atoms or alkyl radicals or form, together with the nitrogen atom to which they are attached, a heterocyclic nucleus or the morpholinyl, piperidinyl, pyrrolidinyl or piperazinyl type, and m is 2 or 3;

$R_3$ denotes a hydrogen atom or a lower alkyl having from 1 to 2 carbon atoms or benzyl radical;

$R_4$ denotes a hydrogen or halogen atom, a lower alkyl radical having from 1 to 5 carbon atoms, a lower alkoxy radical having from 1 to 5 carbon atoms or a trifluoromethyl radical; and n is 1 or 2, and pharmaceutically acceptable acid addition salts.

21. Pharmaceutical preparation for the treatment of vigilance disorders including behavioral disorders attributable to cerebral vascular damage and to cerebral sclerosis in geriatrics comprising at least one of the compounds or salts thereof comprising:

1,2,3,4,5,6-hexahydro-5-hydroxalkylazepino[4,5-b]-indole of formula:

in which $R_1$ denotes a hydrogen atom, a lower alkyl radical having from 1 to 5 carbon atoms, a lower alkenyl radical having from 1 to 5 carbon atoms, a benzyl radical, an alkylamino radical of the formula

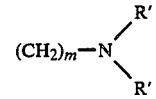

where the groups R' are either hydrogen atoms or lower alkyl radicals having from 1 to 5 carbon atoms or form, together with the nitrogen atom to which they are attached, a heterocyclic nucleus of the morpholinyl, piperidinyl, pyrrolidinyl or piperazinyl type, and m is 2 or 3;

$R_2$ denotes a hydrogen atom or acyl radical of from 1 to 7 carbon atoms;

$R_3$ denotes a hydrogen atom or a lower alkyl having from 1 to 2 carbon atoms or benzyl radical;

$R_4$ denotes a hydrogen or halogen atom, a lower alkyl radical having from 1 to 5 carbon atoms, a lower alkoxy radical having from 1 to 5 carbon atoms or a trifluoromethyl radical; and n is 1 or 2, and pharmaceutically acceptable acid addition salts wherein n=1 including the steps of:

a lower alkoxy radical having from 1 to 5 carbon atoms or a trifluoromethyl radical; and n is 1 or 2, and pharmaceutically acceptable acid addition salts in combination with conventional excipients for permitting oral or parenteral administration.

22. Pharmaceutical preparation according to claim 21, characterized in that it contains the active principle in a dosage ranging from 10 to 100 mg.

* * * * *